United States Patent

O'Brien

Patent Number: 5,884,629
Date of Patent: Mar. 23, 1999

[54] MALE URETHRAL OCCLUSIVE DEVICE

[76] Inventor: Christopher J. O'Brien, P.O. Box 30476, Palm Beach Gardens, Fla. 33420

[21] Appl. No.: 83,988

[22] Filed: May 22, 1998

[51] Int. Cl.[6] .......................................................... A61F 5/48
[52] U.S. Cl. ...................... 128/885; 600/29; 128/DIG. 25
[58] Field of Search ...................... 128/846, 885, 128/886, 842, 844, 918, DIG. 25; 600/29–31; 604/347–353

[56] References Cited

U.S. PATENT DOCUMENTS

| | | | |
|---|---|---|---|
| 5,082,006 | 1/1992 | Jonasson | 128/885 |
| 5,417,226 | 5/1995 | Juma | 128/885 |
| 5,513,659 | 5/1996 | Buuck | 128/885 |
| 5,603,685 | 2/1997 | Tutrone | 128/885 |

*Primary Examiner*—Michael A. Brown
*Attorney, Agent, or Firm*—McHale & Slavin, P.A.

[57] ABSTRACT

The instant invention is a urethral occlusive device designed for insertion into the male urethral opening. The device is effective as a prophylactic and as a male contraceptive device. The device is also useful in treating incontinence and can act as a non-invasive catheter attachment for aiding in the draining of urine from the body.

5 Claims, 1 Drawing Sheet

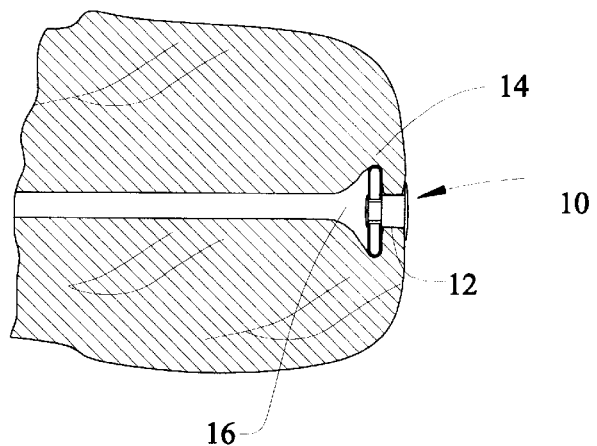
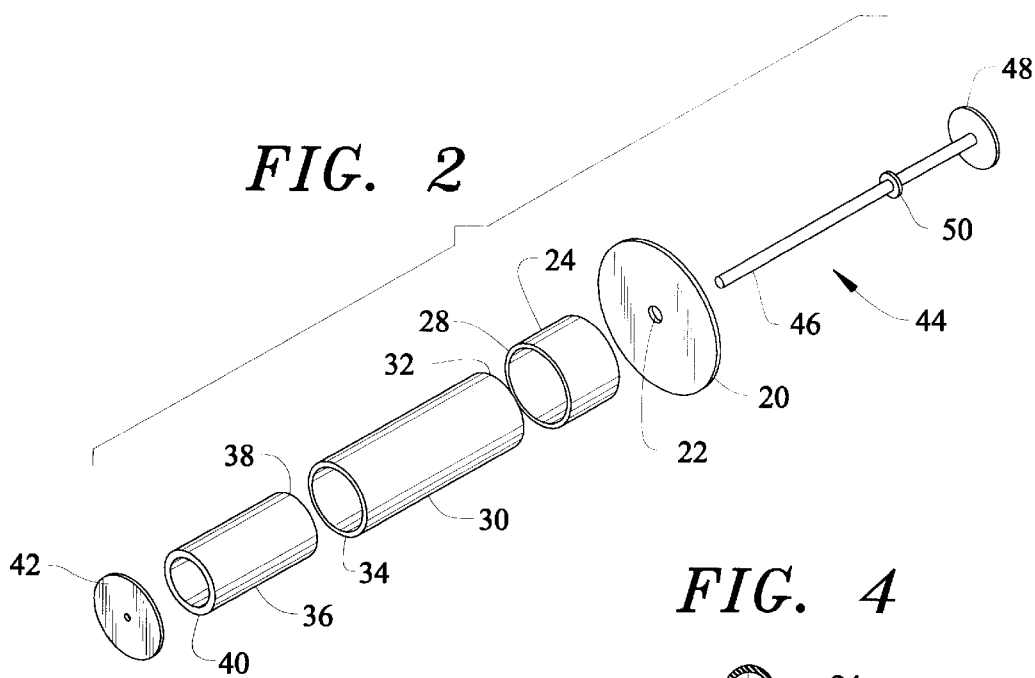
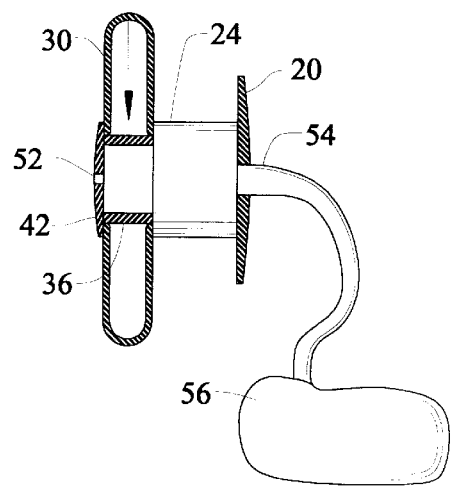
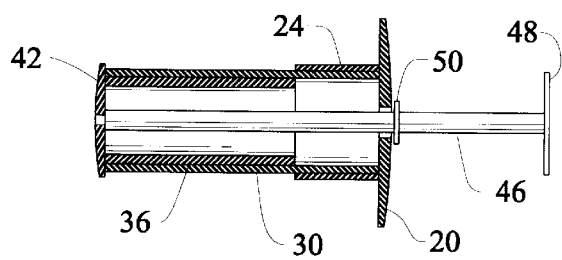

MALE URETHRAL OCCLUSIVE DEVICE

FIELD OF THE INVENTION

This invention relates to occlusive devices for preventing the flow-of bodily fluids from the male urethra.

BACKGROUND OF THE INVENTION

A variety of circumstances make it necessary or desirable to control the flow of bodily fluids from the urethral opening of the male penis. For instance, if contraception is not desired it is imperative that the male spermatozoa be prevented from entering the female vaginal canal. Numerous contraceptive devices are known in the art. The most common of these devices, the condom, is designed to sheath the penis in an impermeable protective covering which acts as a receptacle for ejaculant fluid to prevent unwanted pregnancies, and as a barrier, to prevent ingress or egress of undesirable microbes, such as gonorrhea, herpes, and the AIDS virus. Unfortunately, the use of a condom results in a loss of both spontaneity and sensitivity during intercourse. Additionally, the condom may leak or accidentally fall off, thereby causing infection or unwanted pregnancy.

Additionally, due to the side effects of disease, such as diabetes, or incidental to a surgical procedure, such as removal of the prostate, an adult male may become incontinent. Control of this condition is commonly achieved by wearing absorbent undergarments or, in extreme cases, by use of a urethral catheter and external urine reservoir.

Several devices are known which are designed to occlude either the urethra or the vas deferens.

For example, U.S. Pat. No. 5,474,089 to Waynant teaches a method of reversible sterilization which is accomplished by first inserting a blocking member into a duct in a subject's reproductive system, then altering the dimensions of the blocking member so as to engage and seal the blocking member in the duct and lastly, applying laser irradiation to ablate a portion of the blocking member thereby unblocking the duct. This device requires medical personnel for both the insertion and ablation of the device.

U.S. Pat. No. 4,139,007 to Diamond teaches a method of male contraception that utilizes external pressure applied to the underside of the penis at its base to close the urethral canal, thus preventing the escape of semen. Diamond utilizes a strap and pressure pad combination which must be accurately placed over the urethral canal. Improper placement of the device or accidental displacement thereof will allow semen to flow through the urethra thereby rendering the device inoperative.

U.S. Pat. No. 4,013,063 to Bucalo describes an implant for insertion in the vas deferens which is actuated to a closed position via the appropriate placement of external magnets. The use of this device requires surgical implantation. Furthermore, if the magnets accidentally become dislodged the device returns to the fully open configuration, thereby allowing the flow of spermatozoa through the urethral canal.

U.S. Pat. No. 5,701,914 to Loeffler is directed to a male contraceptive device which is inserted by the user into the urethral canal. Loeffler's device is formed as an expandable body unit having an elastic member covering a plurality of body segments. Upon insertion, the user must depress a small actuator handle which expand the device to block fluids from passing through the urethra. Subsequently, the handle must be further depressed to contract the device and allow for its withdrawal. The device is elliptically shaped and only expands 10% from its original shape. Thus, proper fitting to every male's anatomy is tenuous. Furthermore it requires that inward pressure be exerted in order to expand the device, which can cause the device to become too deeply embedded prior to actuation. Lastly, manipulation of the device requires a great deal of manual dexterity in order that it be utilized effectively.

Thus, what is lacking in the art is a device which can reliably and reversibly occlude the urethral canal. The device must be easily and readily insertable by the user and must be designed for reliable retention. Furthermore, the device should be suitable for retention of all bodily fluids when sealingly engaging the urethral opening.

SUMMARY OF THE INVENTION

The present invention is designed so as to take advantage of the inherent widening of the human male urethra immediately interior of the urethral meatus. When installed the instant device will reversibly prevent the excretion of any bodily fluid from the penis. Initially, the device is in a contracted condition such that two concentrically positioned sections of surgical tubing cooperate to form a flattened area that will occlude the urethral canal when properly positioned. Insertion of an applicator rod to an appropriate depth within the device causes it to stretch to a position where it is easily inserted into the urethral opening. Because the urethra widens immediately interior of the urethral meatus, it defines an internal area suitable for the retention of such an occlusive device. Upon removal of the applicator, the device reverts to its original shape and creates a flattened resilient sealing member which, in cooperation with the outer circular retaining disc, creates an effective occlusive device for prohibiting the flow of any bodily fluids through the urethral opening.

While useful as a male contraceptive device, the instant invention is also well suited for the management of male incontinence. In a particular configuration, the device may be adapted by creation of a continuous central passage for fluid and an exterior receptacle for attachment of a tube. When used in this configuration, the device becomes a non-invasive urethral catheter.

Thus, it is an objective of the instant invention to provide an occlusive device for insertion in the urethral opening of a male penis to provide a prophylactic effect.

It is a further objective of the instant invention to provide a urethral occlusive device capable of providing a contraceptive effect.

It is yet an additional objective of the invention to provide a urethral occlusive device capable of controlling the flow of urine so as to control incontinence.

It is still another objective of the invention to provide a urethral occlusive device adapted to attach to a catheter and provide a non-invasive means for catheter attachment.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1 is a cross-sectional view of a male penis showing the occlusive device inserted within the urethral opening.

FIG. 2 is an exploded view of the occlusive device.

FIG. 3 is a cross-sectional view of the occlusive device in its extended position prior to insertion.

FIG. 4 is a cross-sectional view of the occlusive device in its collapsed position.

DETAILED DESCRIPTION OF THE PREFERRED EMBODIMENT

Now referring to FIG. 1, a urethral occlusive device 10 is shown inserted into the urethral opening 12 in the meatal tissue area 14 of a male urethra 16.

Referring to FIG. 2, a first circular retaining disc 20 is shown having a central opening 22 and being of a diameter sufficiently large so as to provide an external restraint which prevents the device from entirely entering the urethra. A space maintaining member 24 is provided having an annular cross section and being of a diameter less than the retaining disc, the space maintaining member having a proximal end 26 and a distal end 28, the proximal end being attached to the retaining disc and concentric therewith, the member being constructed of a material selected from the group consisting of surgical grade rubber or silicone which has sufficient rigidity so as to prevent restriction of the meatal tissue.

The device includes an occlusive assembly having a first extensible member 30 and a second extensible member 36, the members each being constructed of a material selected from the group consisting of surgical grade rubber or silicone. The first extensible member is characterized by an annular segment having a proximal end 32 and a distal end 34 and having a diameter less than the outer diameter of the space maintaining member. The second extensible member 36 is characterized by an annular segment having a proximal end 38 and a distal end 40 and having a diameter less than the internal diameter of the first extensible member. The proximal ends of the first and second extensible members are attached to the distal end of the space maintaining member and are concentric therewith.

The device further includes a second circular retaining disc 42 having a diameter substantially equal to the space maintaining member and being attached to the distal ends of the first and second extensible members and concentric therewith. An applicator assembly 44 is further described and is characterized by a shaft 46 having a knob 48 at its proximal end and a retaining ridge 50 particularly disposed along the length of the shaft. The shaft is constructed and arranged so that the distal end thereof is readily inserted into the central opening of the first retaining disc. Upon insertion of the applicator assembly into the first retaining disc with sufficient pressure, the retaining ridge engages the central opening of the first retaining disc and precisely extends the extensible members to an optimum length so as to define a minimum diameter and thereby facilitate insertion.

This configuration is best described by FIG. 3, wherein the second extensible member 36 has been stretched to a point so that the first extensible member 30 has been pulled taught and defines a substantially parallel outer wall. Upon extraction of the applicator assembly the extensible members revert to their original configuration, as best shown in FIG. 4 such that the second extensible member 36 retracts and causes flattening of the first extensible member 30 to create an internal seal within the urethral opening juxtaposed the space maintaining member 24. In this position, the first circular retaining disc 20 and the first extensible member 30 cooperate so as to sealingly engage the meatal tissue surrounding the urethral opening and create a closure which prevents the passage of bodily fluids.

In a particularly preferred embodiment, a central opening 52 may optionally be created in the second circular retaining disc 42 so as to allow for the flow of urine through the device and through a catheter 54 which engages the first retaining disc. The urine is then directed to an external reservoir 56. This configuration allows for non-invasive catheterization whereby it is not necessary to thread a catheter all the way into the bladder. By utilizing this technique, it is possible to avoid trauma to the entire urethra and bladder which is sometimes caused by invasive catheterization. Additionally, the possibility of infection that often occurs due to invasive catheterization is avoided.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

What is claimed is:

1. A urethral meatus occlusive device for insertion through a meatal tissue area in a male urethra comprising: a first circular retaining disc having a central opening and being of a diameter sufficiently large to provide an external restraint thereby preventing the device from entirely entering the urethra;

a space maintaining member of annular cross section having a diameter less than said retaining disc, said member having a proximal end and a distal end, said proximal end being attached to said retaining disc and concentric therewith, said member being formed of a material selected from the group consisting of surgical grade rubber or silicone and having sufficient rigidity so as to prevent restriction of the meatal tissue;

an occlusive assembly having a first extensible member and a second extensible member, said members each being formed of a material selected from the group consisting of surgical grade rubber or silicone, said first extensible member characterized by an annular segment having a proximal end and a distal end and having a diameter less than the outer diameter of said space maintaining member, said second extensible member characterized by an annular segment having a proximal end and a distal end and having an outer diameter less than the internal diameter of said first extensible member, said proximal ends of said first and second extensible members being attached to said distal end of said space maintaining member and concentric therewith;

a second circular retaining disc having a diameter substantially equal to said space maintaining member and being attached, to said distal ends of said first and second extensible members and concentric therewith; and an applicator assembly characterized by a shaft having a knob at its proximal end and a retaining ridge particularly disposed along the length of the shaft, said shaft being constructed and arranged so that the distal end thereof is readily inserted into the central opening of the first retaining disc;

whereby, upon insertion of the applicator assembly into the first retaining disc with sufficient pressure, said retaining ridge engages said central opening of said first retaining disc and precisely extends said extensible members to an optimum length so as to define a minimum diameter and thereby facilitate insertion and upon subsequent extraction of said applicator assembly said extensible members revert to their original configuration such that said second extensible member retracts to cause flattening of said first extensible member thereby creating an internal seal within the urethral opening juxtaposed said space maintaining member.

2. The occlusive device according to claim 1 wherein the second circular retaining disc contains a central opening, whereby bodily fluids are permitted to flow through said opening.

3. A method of catheterization comprising: providing a urethral occlusive device as set forth in claim 2; sealingly engaging said device within the urethral opening; sealingly engaging a catheter within the central opening of said first circular retaining disc; and directing the flow of urine to an external reservoir.

4. A method of male contraception comprising: providing a urethral occlusive device as set forth in claim 1; and sealingly engaging said device within the urethral opening prior to sexual intercourse.

5. A method of managing incontinence comprising: providing a urethral occlusive device as set forth in claim 1; and sealingly engaging said device within the urethral opening.

* * * * *